US012599769B2

(12) United States Patent
Kim et al.

(10) Patent No.: US 12,599,769 B2
(45) Date of Patent: Apr. 14, 2026

(54) BALLOON-TYPE RETINAL STIMULATION DEVICE AND METHOD FOR MANUFACTURING SAME

(71) Applicant: DAEGU GYEONGBUK INSTITUTE OF SCIENCE AND TECHNOLOGY, Daegu (KR)

(72) Inventors: So Hee Kim, Daegu (KR); Hyun Min Moon, Daegu (KR); Nam Sun Chou, Seoul (KR)

(73) Assignee: DAEGU GYEONGBUK INSTITUTE OF SCIENCE AND TECHNOLOGY, Daegu (KR)

( * ) Notice: Subject to any disclaimer, the term of this patent is extended or adjusted under 35 U.S.C. 154(b) by 296 days.

(21) Appl. No.: 18/367,566

(22) Filed: Sep. 13, 2023

(65) Prior Publication Data

US 2024/0001118 A1     Jan. 4, 2024

Related U.S. Application Data

(62) Division of application No. 16/770,327, filed as application No. PCT/KR2018/014999 on Nov. 29, 2018, now Pat. No. 11,771,896.

(30) Foreign Application Priority Data

Dec. 6, 2017    (KR) ........................ 10-2017-0166674

(51) Int. Cl.
*A61N 1/36*         (2006.01)
*A61B 5/24*         (2021.01)
                        (Continued)

(52) U.S. Cl.
CPC ............ *A61N 1/36046* (2013.01); *A61B 5/24* (2021.01); *A61F 9/00781* (2013.01);
                        (Continued)

(58) Field of Classification Search
CPC .............. A61N 1/36046; A61N 1/0543; A61F 2240/001
See application file for complete search history.

(56) References Cited

U.S. PATENT DOCUMENTS 11,771,896 B2 *  10/2023  Kim ..................... A61N 1/0543
                                                            607/53
2009/0018630 A1 *  1/2009  Osypka ................ A61N 1/0558
                                                            607/116
(Continued)

FOREIGN PATENT DOCUMENTS

JP           4130589         8/2008
KR    10-2003-0035738        5/2003
                (Continued)

*Primary Examiner* — Eric D. Bertram
(74) *Attorney, Agent, or Firm* — LEX IP MEISTER, PLLC

(57) ABSTRACT

A balloon type retinal stimulation device includes: a substrate unit having an insertion portion provided to be inserted into an eyeball; and a stimulation unit that is provided at one or both of one and the other surfaces of the substrate unit. The insertion portion is provided to be expandable and contractible as a fluid is injected into and discharged from an inside of the injection portion. When the insertion portion expands, one surface of the insertion portion is deformed to match a shape of the retina such that the stimulation unit is brought into close contact with the retina on which an image is formed, and the other surface of the insertion portion comes into close contact with an inner surface of the eyeball that is not a region of retina on which an image is formed, to support the insertion portion that is in contact with the region of retina on which an image is formed.

10 Claims, 10 Drawing Sheets

(51) Int. Cl.
   *A61F 9/007*        (2006.01)
   *A61N 1/05*         (2006.01)
   *A61N 1/08*         (2006.01)

(52) U.S. Cl.
   CPC ............. *A61N 1/0543* (2013.01); *A61N 1/08*
      (2013.01); *A61F 2240/001* (2013.01); *A61F*
         *2250/0003* (2013.01); *A61F 2250/0013*
                              (2013.01)

(56)                    References Cited

U.S. PATENT DOCUMENTS

| | | | | |
|---|---|---|---|---|
| 2010/0265680 A1* | 10/2010 | Tai | ..................... | A61B 5/0031 |
| | | | | 29/825 |
| 2012/0109255 A1* | 5/2012 | Fan | ..................... | A61N 1/0543 |
| | | | | 607/54 |
| 2015/0018901 A1* | 1/2015 | Li | ..................... | A61N 5/0622 |
| | | | | 607/92 |
| 2016/0256677 A1* | 9/2016 | Song | ..................... | A61N 1/0543 |
| 2017/0319092 A1* | 11/2017 | Wendel-Mitoraj | ....... | A61N 1/05 |

FOREIGN PATENT DOCUMENTS

| | | |
|---|---|---|
| KR | 10-1253334 | 4/2013 |
| KR | 10-1559568 | 10/2015 |
| KR | 10-2017-0086136 | 7/2017 |

* cited by examiner

STEP OF PREPARING LOWER SUBSTRATE
AND UPPER SUBSTRATE — S210

STEP OF PERFORMING ADHESION OF PREPARED
UPPER SUBSTRATE AND LOWER SUBSTRATE — S220

STEP OF FORMING METAL ELECTRODE LAYER
OVER ADHESION-PERFORMED UPPER SUBSTRATE — S230

STEP OF FORMING INSULATION LAYER ON
METAL ELECTRODE LAYER — S240

STEP OF REMOVING CARRIER SUBSTRATE
INCLUDED IN LOWER SUBSTRATE — S250

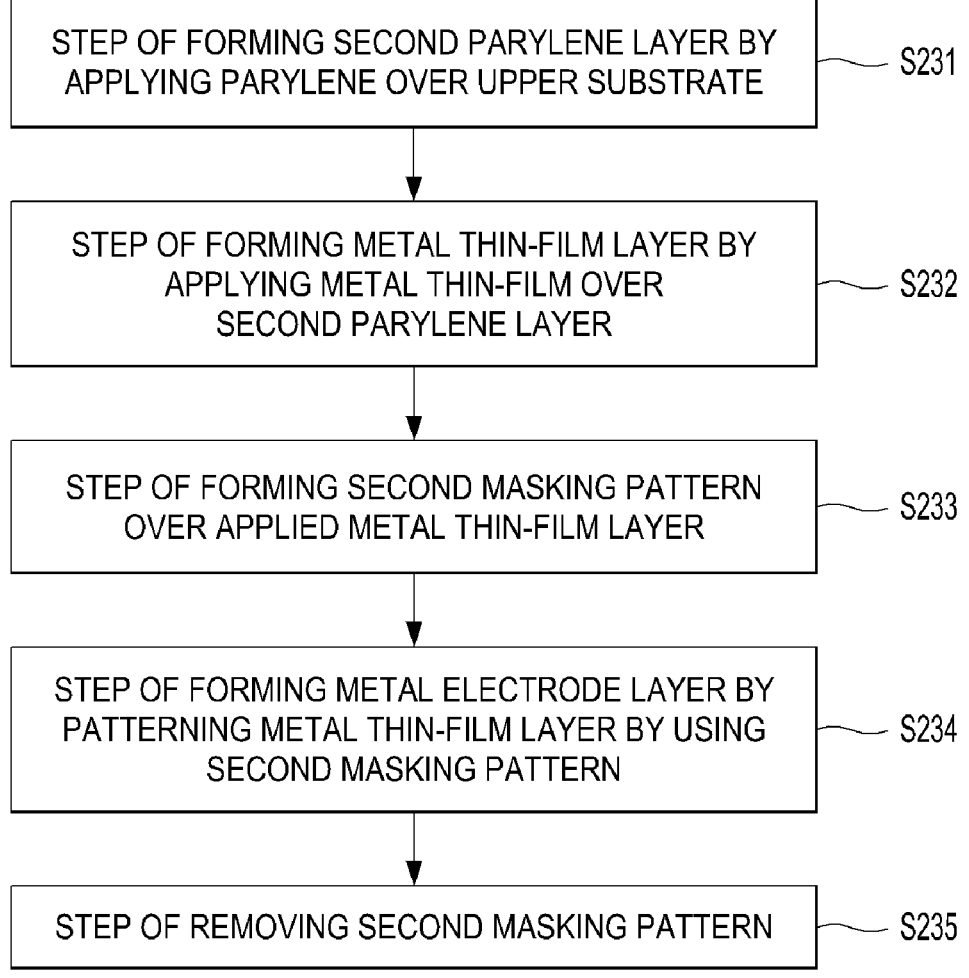

STEP OF FORMING SECOND PARYLENE LAYER BY APPLYING PARYLENE OVER UPPER SUBSTRATE — S231

STEP OF FORMING METAL THIN-FILM LAYER BY APPLYING METAL THIN-FILM OVER SECOND PARYLENE LAYER — S232

STEP OF FORMING SECOND MASKING PATTERN OVER APPLIED METAL THIN-FILM LAYER — S233

STEP OF FORMING METAL ELECTRODE LAYER BY PATTERNING METAL THIN-FILM LAYER BY USING SECOND MASKING PATTERN — S234

STEP OF REMOVING SECOND MASKING PATTERN — S235

FIG. 6

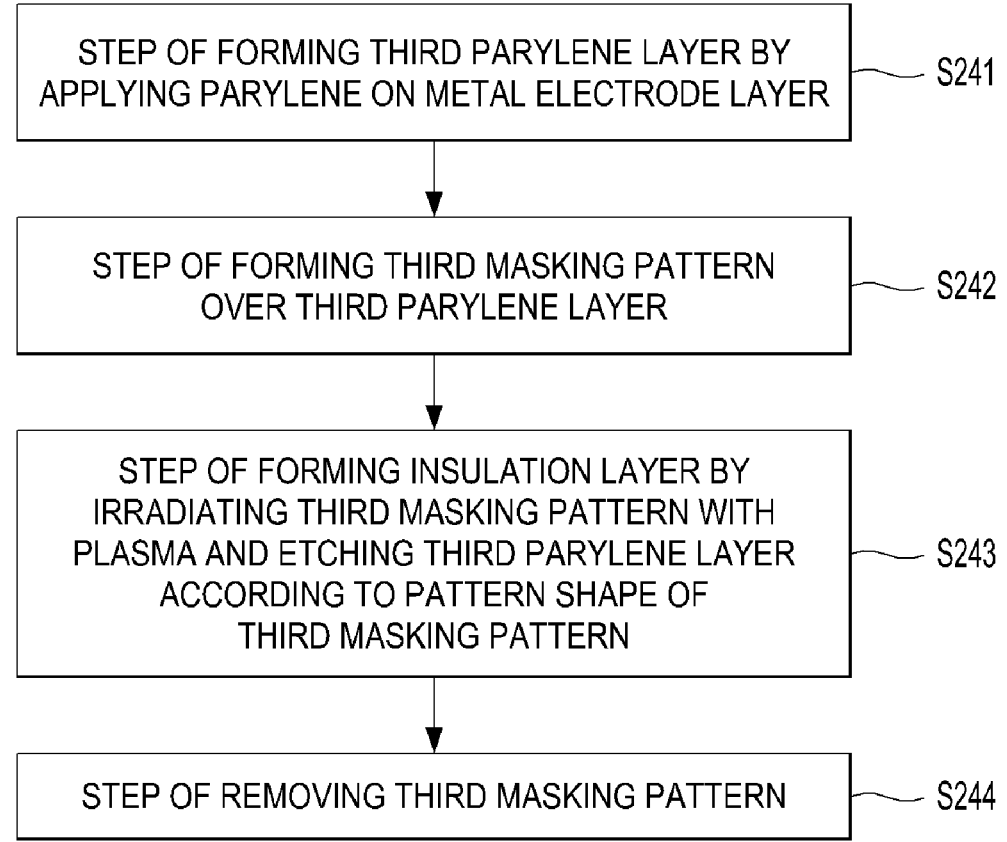

| | |
|---|---|
| STEP OF FORMING THIRD PARYLENE LAYER BY APPLYING PARYLENE ON METAL ELECTRODE LAYER | S241 |
| STEP OF FORMING THIRD MASKING PATTERN OVER THIRD PARYLENE LAYER | S242 |
| STEP OF FORMING INSULATION LAYER BY IRRADIATING THIRD MASKING PATTERN WITH PLASMA AND ETCHING THIRD PARYLENE LAYER ACCORDING TO PATTERN SHAPE OF THIRD MASKING PATTERN | S243 |
| STEP OF REMOVING THIRD MASKING PATTERN | S244 |

FIG. 8

BALLOON-TYPE RETINAL STIMULATION DEVICE AND METHOD FOR MANUFACTURING SAME

CROSS-REFERENCE TO RELATED APPLICATIONS

This application claims the benefit of Korean Patent Application No. 10-2017-0166674, filed Dec. 6, 2017, which issued as Korean Patent No. KR 10-2095437 B1. This application is a divisional of U.S. patent application Ser. No. 16/770,327, filed on Jun. 5, 2020, now U.S. Pat. No. 11,771,896. This application is also related to International Patent Application No. PCT/KR2018/014999, filed on Nov. 29, 2018, published as WO 2019/112246 A2. The entire disclosures of the foregoing applications and patents are hereby incorporated by reference in their entireties.

BACKGROUND/SUMMARY

Technical Field

The present invention relates to a balloon type retinal stimulation device and a method for manufacturing the same, and more specifically, to a balloon type retinal stimulation device that enables an incision area in outer layers including sclera and choroid to become minimized, can come into close contact with a region of retina of an eyeball on which an image is formed so as to stably apply electrical stimulation to the retina or stably measure an electrical signal from the retina, and a method for manufacturing the balloon type retinal stimulation device.

Background Art

In general, an electrical stimulation device for a retina is configured to form an artificial retina by performing incision in outer layers to insert an electrode into an incision site and then attaching the inserted electrode to the retina.

In addition, since a retinal stimulation device in the related art makes it difficult, due to its thickness, for an electrode substrate to come into close contact with the retina along a curve thereof, problems arise in that the electrode does not come into close contact with the retina depending on a size of an eyeball or a curve of retina which is different for each person, and the electrode is easily detached as a patient's head moves during a medical procedure or the patient's activity.

Besides, as described above, when the electrode does not come into close contact with the retina, it is not possible to accurately apply electrical stimulation to a desired site.

Consequently, in the related art, in order to prevent the electrode from moving without coming into close contact with the retina, the electrode needs to be fixed using an additional device after the retinal stimulation device is attached. However, when the retinal stimulation device is attached using an additional device as described above, problems arise in that time for a medical procedure increases, manufacturing costs increases uneconomically, and long-term implantation is hardly achieved.

Consequently, it is necessary to provide a retinal stimulation device having a structure that can be applied to a procedure even for a different size of an eyeball, can be easily fixed without a damage to a biological tissue, and can achieve long-term implantation.

<Prior Patent Literature> Japanese Patent No. 4130589

SUMMARY OF INVENTION

Technical Problem

Objects of the present invention to solve such problems described above are to provide a balloon type retinal stimulation device that enables an incision area in outer layers to become minimized and can come into close contact with a region of retina in an inside of an eyeball on which an image is formed such that electrical stimulation can be stably applied to the retina, and a method for manufacturing the balloon type retinal stimulation device.

Technical objects to be achieved by the present invention are not limited to the technical objects mentioned above, and the following description enables other unmentioned technical objects to be clearly understood by a person of ordinary skill in the art to which the present invention belongs.

Solution to Problem

According to a configuration of the present invention to achieve an object described above, there is provided a balloon type retinal stimulation device including: a substrate unit having an insertion portion provided to be inserted into an eyeball; and a stimulation unit that is provided at one or both of one and the other surfaces of the substrate unit. The insertion portion is provided to be expandable and contractible as a fluid is injected into and discharged from an inside of the injection portion. When the insertion portion expands, one surface of the insertion portion is deformed to match a shape of the retina such that the stimulation unit is brought into close contact with the retina on which an image is formed, and the other surface of the insertion portion comes into close contact with an inner surface of the eyeball that is not a region of retina on which an image is formed, to support the insertion portion that is in contact with a region of retina on which an image is formed.

In an embodiment of the present invention, the balloon type retinal stimulation device may further include a circuit unit that is coupled to the substrate unit and has an IC chip connected to the stimulation unit.

In the embodiment of the present invention, the substrate unit may further have a chip installed portion that is provided to be extended from the insertion portion and is coupled to the circuit unit.

In the embodiment of the present invention, the stimulation unit may have one or more cables provided to be extended from the IC chip to the insertion portion; and one or more stimulation portions that are positioned on the insertion portion.

In the embodiment of the present invention, the stimulation portion may be configured of one or more of sensors and electrodes and may be provided to be able to electrically stimulate the retina. In addition, the stimulation portion may be used for measuring an electrical signal of the retina, as necessary.

In the embodiment of the present invention, the insertion portion may be formed to have a thickness different for each of both surfaces thereof.

In the embodiment of the present invention, the insertion portion may be provided to expand and contract a volume thereof so as to adjust intraocular pressure of a patient.

In the embodiment of the present invention, the substrate unit may further have a fixing portion which is formed to be extended around a circumference of the insertion portion and which is provided not to expand. The fixing portion may be provided to come into contact with an inner surface of the eyeball that is not the region of retina on which the image is formed so as to fix the stimulation unit, when the insertion portion expands.

According to another configuration of the present invention to achieve the other object described above, there is provided a method for manufacturing a balloon type retinal stimulation device, including: a) a step of preparing a lower substrate, an adhesion layer, and an upper substrate; b) a step of performing adhesion of the prepared upper substrate and lower substrate; c) a step of forming a metal electrode layer over the adhesion-performed upper substrate; and d) a step of forming an insulation layer on the metal electrode layer.

In an embodiment of the present invention, in the step a), the lower substrate may be provided to be prepared by forming a first polydimethylsiloxane (PDMS) spin-coated layer over a carrier substrate and forming a first Parylene layer by applying Parylene over the first spin-coated PDMS layer, and the upper substrate may be provided to be prepared by forming a second spin-coated PDMS layer over the first Parylene layer.

In the embodiment of the present invention, the step b) may include: b1) a step of forming first masking patterns over the prepared upper substrate; b2) a step of irradiating the first masking patterns with plasma; and b3) a step of removing the first masking patterns.

In the embodiment of the present invention, in the step b1), the first masking patterns may be formed as patterns at sites where the upper substrate and the lower substrate are not bonded to each other.

In the embodiment of the present invention, in the step b2), the plasma with which irradiation is performed to the first masking patterns may cause the first Parylene layer positioned at an outer side of the first masking patterns to adhere to the upper substrate.

In the embodiment of the present invention, the step of c) may include: c1) a step of forming a second Parylene layer by applying Parylene over the upper substrate; c2) a step of forming a metal thin-film layer by applying a metal thin-film over the second Parylene layer; c3) a step of forming second masking patterns over the applied metal thin-film layer; c4) a step of forming the metal electrode layer by patterning the metal thin-film layer by using the second masking patterns; and c5) a step of removing the second masking patterns.

In the embodiment of the present invention, in the step c4), the metal thin-film layer is provided to be patterned into a preset pattern by performing a wet etching process according to pattern shapes of the second masking patterns.

In the embodiment of the present invention, in the step c4), the metal thin-film layer is provided to be patterned into a preset pattern by performing a lift-off process according to pattern shapes of the second masking patterns.

In the embodiment of the present invention, the step of d) may include: d1) a step of forming a third Parylene layer by applying Parylene on the metal electrode layer; d2) a step of forming third masking patterns over the third Parylene layer; d3) a step of forming the insulation layer by irradiating the third masking patterns with plasma and etching the third Parylene layer according to pattern shapes of the third masking patterns; and d4) a step of removing the third masking patterns.

In the embodiment of the present invention, in the step of d3), the third masking patterns are irradiated with O.sub.2 plasma.

In the embodiment of the present invention, the method for manufacturing a balloon type retinal stimulation device may further include e) a step of removing a carrier substrate included in the lower substrate, after the step d).

Advantageous Effects of Invention

According to configurations described above, effects of the present invention are as follows. A stimulation unit can come into close contact with a retina to stably apply electrical stimulation to the retina at a predetermined position or to measure an electrical signal of the retina.

In addition, according to the present invention, an insertion portion of a substrate unit is inserted into an eyeball in a contracted state, and thus an incision area in outer layers can be minimized. As described above, when the incision area in the outer layers is small, it is possible to prevent the occurrence of problems of bacterial penetration and infection into an incision site during or after a medical procedure, and a patient can quickly recover after the medical procedure.

Besides, the insertion portion is provided to expand in a state of being completely inserted into an eyeball. Here, one surface of the insertion portion is deformed to match a shape of the retina such that the stimulation unit is brought into close contact with the retina on which an image is formed, and the other surface of the insertion portion comes into close contact with an inner surface of the eyeball that is not a region of retina on which an image is formed, to support the insertion portion that is in contact with a region of retina on which an image is formed. Consequently, when a patient's head moves, or even when the patient does activity, there is no risk of detachment of the stimulation unit from the retina, and thus the present invention can be stably used.

In addition, the substrate unit is made of an elastomer material and expands into a flexible balloon shape, and thus shape compensation can be easily made depending on movement of the eyeball. Consequently, even when the substrate unit according to the present invention is stably inserted into the eyeball for a long time, it is possible for the retina not to be damaged.

In addition, a balloon type retinal stimulation device according to the present invention is conveniently used since a circuit unit is provided to be integrally attached to the substrate unit so as to measure an electrical signal of the retina and apply electrical stimulation to the retina without an additional device.

In addition, according to the present invention, the insertion portion of the balloon type retinal stimulation device can contract and expand to also adjust intraocular pressure of a patient.

The effects of the present invention are construed not to be limited to the above-mentioned effects but to include every effect that can be derived from the configurations of the invention described in the detailed description of the embodiments or claims of the present invention.

BRIEF DESCRIPTION OF DRAWINGS

FIG. 6 is a flowchart of a step of forming a metal electrode layer according to the embodiment of the present invention.

FIG. 8 is a flowchart of a step of forming an insulation layer according to the embodiment of the present invention.

DESCRIPTION OF EMBODIMENTS

Hereinafter, the present invention will be described with reference to the accompanying drawings. However, the present invention can be realized as various different examples, thus not being limited to embodiments described here. Besides, parts irrelevant to the description are omitted from the drawings in order to clearly describe the present invention, and similar reference signs are assigned to similar parts through the entire specification.

In the entire specification, a case where a certain part "is connected to (accesses, is in contact with, or is coupled to)" another part includes not only a case where the parts are "directly connected" to each other, but also a case where the parts are "indirectly connected" to each other with another member interposed therebetween. In addition, a case where a certain part "includes" a certain configurational element means a case where another configurational element is not excluded but can be further included, unless specifically described otherwise.

Terms used in this specification are only used to describe a specific embodiment and are not intentionally used to limit the present invention thereto. A word having a singular form contain a meaning of its plural forms, unless obviously implied otherwise in context. In this specification, words such as "to include" or "to have" are construed to specify that a feature, a number, a step, an operation, a configurational element, a member, or a combination thereof described in the specification is present and not to exclude presence or a possibility of addition of one or more other features, numbers, steps, operations, configurational elements, members, or combinations thereof in advance.

Hereinafter, embodiments of the present invention will be described in detail with reference to the accompanying drawings.

Figure 1:
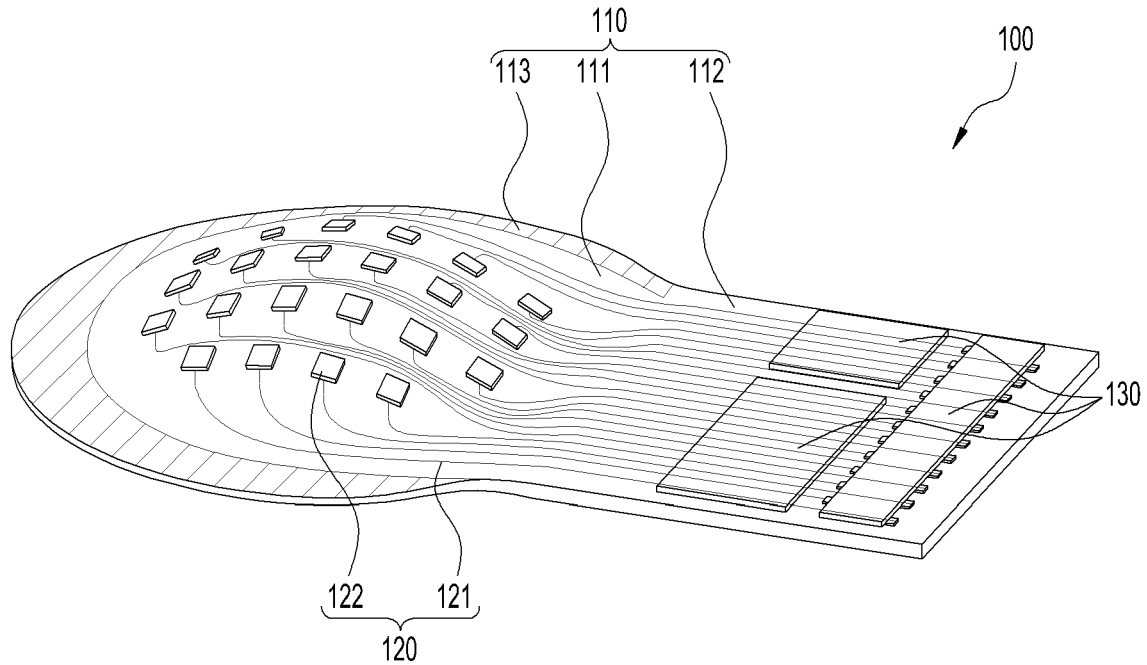
FIG. 1 is a perspective view of a balloon type retinal stimulation device according to an embodiment of the present invention.
Figure 2:
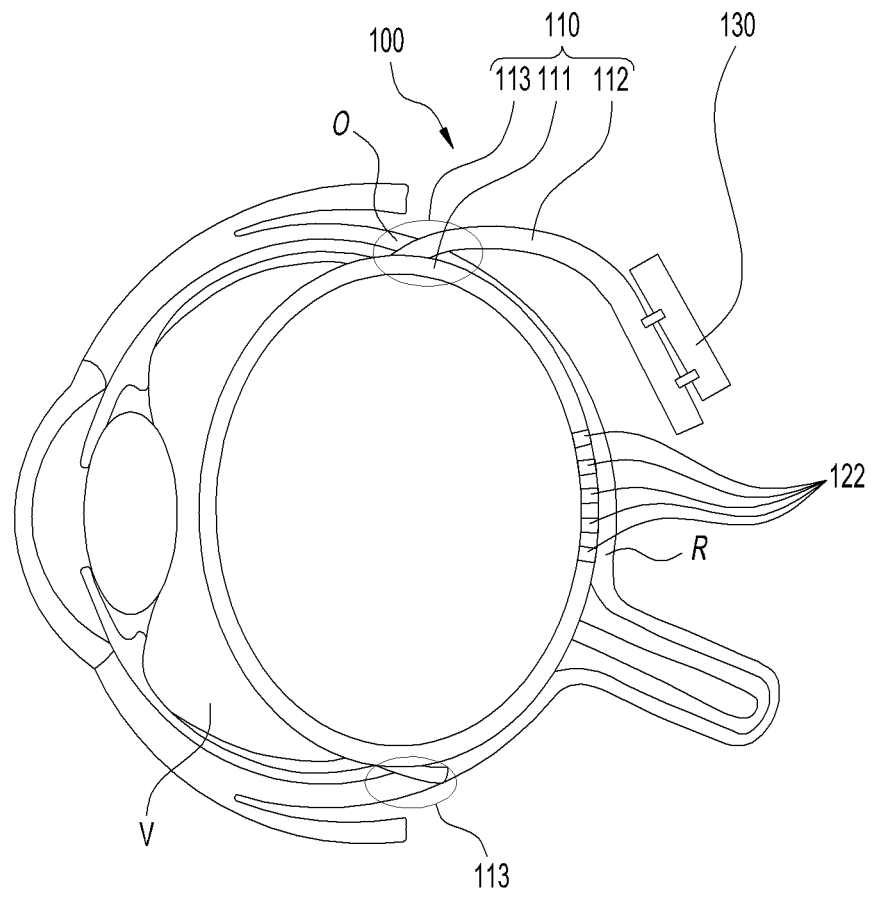
FIG. 2 is a view illustrating an operation representing a state where the balloon type retinal stimulation device according to the embodiment of the present invention is inserted into an eyeball.

FIG. 1 is a perspective view of a balloon type retinal stimulation device according to an embodiment of the present invention, and FIG. 2 is a view illustrating an operation representing a state where the balloon type retinal stimulation device according to the embodiment of the present invention is inserted into an eyeball.

As illustrated in FIGS. 1 and 2, the balloon type retinal stimulation device 100 includes a substrate unit 110, a stimulation unit 120, and a circuit unit 130.

The substrate unit 110 includes an insertion portion 111, a chip installed portion 112 and a fixing portion 113.

The insertion portion 111 is provided to be inserted into the eyeball and can be provided to expand and contract.

Specifically, the insertion portion 111 can be provided to be expandable and contractible as a fluid is injected into and discharged from an inside of the injection portion. When the insertion portion 111 expands, one surface of the insertion portion is deformed to match a shape of the retina R such that the stimulation unit 120 is brought into close contact with the retina R on which an image is formed, and the other surface of the insertion portion 111 comes into close contact with an inner surface of the eyeball except the region of retina R on which an image is formed. Here, in the present invention, the inner surface of the eyeball except the region of retina R can refer to a surface at which the one surface of the insertion portion 111 comes into contact with vitreous humor V.

Consequently, according to the present invention, even when a patient's head moves, there is no risk of detachment of the stimulation unit 120 from the retina, and thus the balloon type retinal stimulation device is stably used.

In addition, the insertion portion 111 can be provided to have the same or different thickness at both surfaces.

In addition, when the insertion portion 111 expands to fix the electrode, the one surface of the insertion portion 111 that comes into contact with the retina R may be formed to be thinner than the other surface of the insertion portion 111 that comes into contact with the inner surface of the eyeball. Specifically, when the insertion portion 111 expands, the one surface of the insertion portion 111 that comes into contact with the retina R needs to be flexibly deformed to match a shape of the retina R. On the other hand, the other surface of the insertion portion 111 that comes into contact with the inner surface of the eyeball needs to come into contact with the inner surface of the eyeball except the region of retina on which an image is formed so as to support the substrate unit 110 such that the substrate unit does not move. Consequently, the one surface of the insertion portion 111 that comes into contact with the retina R can be formed to be thinner than the other surface of the insertion portion 111 that comes into contact with the inner surface of the eyeball except the region of retina R on which an image is formed.

Besides, the insertion portion 111 can be made of an elastomer material. Consequently, the insertion portion 111 expands into a flexible balloon shape, and thus shape compensation can be easily made following movement of a connected cable. Consequently, even when the substrate unit 110 according to the present invention is stably inserted into the eyeball for a long time, it is possible to not damage the retina R. However, a material of the insertion portion 111 is not limited to an elastomer, and examples of materials include every material that can have an effect similar to that of the elastomer.

The insertion portion 111 provided as described above can be in a contracted state when being inserted into the eyeball, and the insertion portion 111 can be provided to expand when being completely inserted into a preset position.

At this point, the outer layer O can be in a state of being incised by a size which only allows the insertion portion 111 to pass.

In other words, according to the present invention, the insertion portion 111 of the substrate unit 110 is inserted into the eyeball in a contracted state, and thus an incision area in the outer layer O can be minimized. As described above, when the incision area in the outer layer O is small, it is possible to prevent the occurrence of problems of bacterial penetration and infection into an incision site during or after a medical procedure, and a patient can quickly recover after the medical procedure.

In addition, the fixing portion 113 can be formed to be extended around a circumference of the insertion portion 111 and, unlike the insertion portion 111, can be provided not to expand. The fixing portion 113 provided as described above can be provided, when the insertion portion 111 expands, to fix the stimulation unit 120 by causing the stimulation unit to come into close contact with the region of retina R on which an image is formed.

Specifically, the insertion portion 111 is provided to have an inner side which expands and contracts, and the fixing portion 113 formed to be extended around an outer circumference of the insertion portion 111 is provided not to expand and contract. The fixing portion 113 provided as described above curves as the insertion portion 111 expands. Consequently, when the insertion portion 111 expands, the fixing portion 113 comes into close contact with the inner surface of the eyeball that is not the region of retina to function as an anchor, thereby causing the stimulation unit 120 to be firmly fixed.

In addition, the insertion portion 111 of the balloon type retinal stimulation device 100 can contract and expand to even adjust the intraocular pressure. In other words, when a patient has high intraocular pressure, a fluid in the insertion portion 111 is discharged to contract the insertion portion 111, and thereby it is possible to decrease the intraocular pressure. Conversely, when a patient has low intraocular pressure, a fluid is injected into the insertion portion 111 to expand the insertion portion 111, and thereby it is possible to increase the intraocular pressure.

The insertion portion 111 provided as described above comes into close contact with the retina R with appropriate pressure and thus can be fixed without a damage to a biological tissue.

In addition, similarly to a balloon, the insertion portion 111 can expand and contract depending on injection and discharge of the fluid, thus it is possible to save costs in that the insertion portion can be fixed regardless of a size of the eyeball different for each person.

The chip installed portion 112 can be provided to be extended from the insertion portion 111 and can have a configuration in which the circuit unit 130 is coupled thereto.

Specifically, the chip installed portion 112 can be provided such that when the insertion portion 111 is inserted into the retina R and the eyeball, the chip installed portion 112 is positioned outside the outer layer O, and one or more circuit units 130 can be installed at the chip installed portion.

The stimulation unit 120 can be provided at one or both of one surface and the other surface of the substrate unit 110 and has cables 121 and stimulation portions 122.

The cable 121 can be provided to be extended from an IC chip of the circuit unit 130 to the insertion portion 111.

At this point, the cables 121 can be provided to correspond one-to-one to the stimulation portions 122 such that the cables 121 can be connected to the respective stimulation portions 122.

The stimulation unit 120 provided as described above allows a current to flow only to the cable 121 connected to the stimulation portion 122 at a position to which electrical stimulation is to be applied, thereby being capable of more finely controlling a position to which the electrical stimulation is applied.

In addition, one or more of the stimulation portions 122 can be provided in a length direction of the cables 121 positioned on the insertion portion 111. In addition, the stimulation portions 122 can be configured of one or more of sensors and electrodes and can be provided to electrically stimulate the retina R. Furthermore, the stimulation portion 122 can be provided to measure an electrical signal of the retina R.

When the insertion portion 111 expands, the stimulation portions 122 provided as described above can come into close contact with the retina R to stably apply the electrical stimulation to the retina at a predetermined position.

The circuit unit 130 can be provided to be coupled to the substrate unit 110 and have IC chips connected to the stimulation unit 120. The balloon type retinal stimulation device 100 provided as described above is conveniently used by having the circuit unit 130 that is provided to be integrally attached to the substrate unit 110 so as to measure the electrical signal of the retina R and apply the electrical stimulation to the retina R without an additional device.

In addition, the circuit unit 130 can be provided to be capable of performing wireless communication so as to perform post-processing of the electrical signal. In other words, the circuit unit 130 transmits an electrical signal of the retina to the optic nerve and enables the balloon type retinal stimulation device 100 to fulfill a function of an artificial retina.

Figure 3:
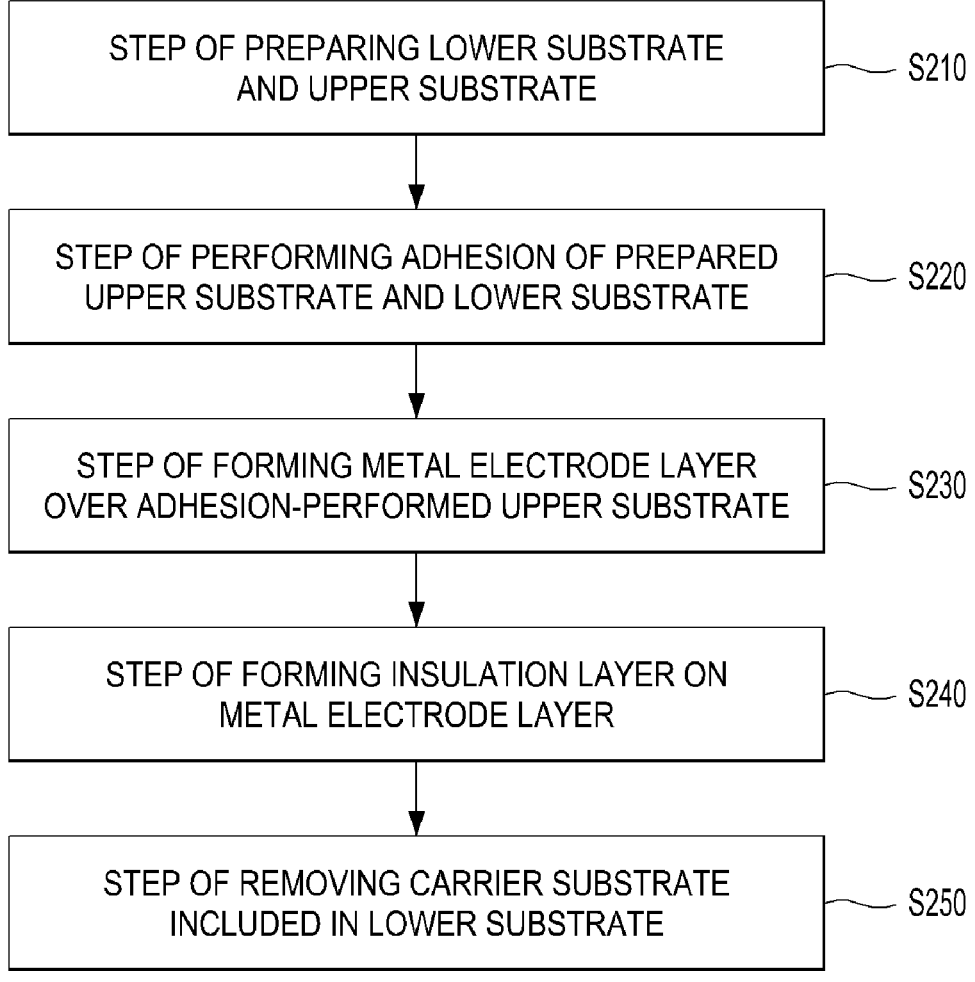
FIG. 3 is a flowchart of a method for manufacturing the balloon type retinal stimulation device according to the embodiment of the present invention.
Figure 4:
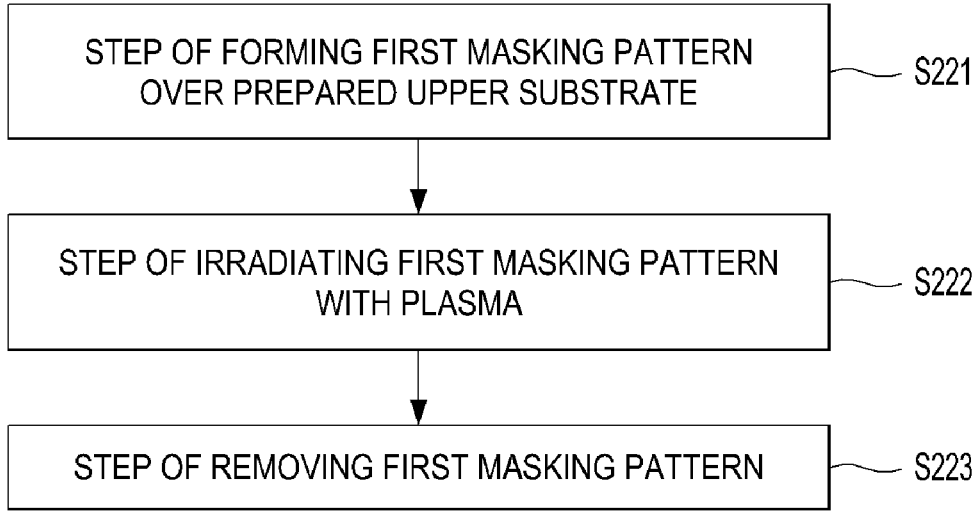
FIG. 4 is a flowchart of a step of performing adhesion according to the embodiment of the present invention.
Figure 5:
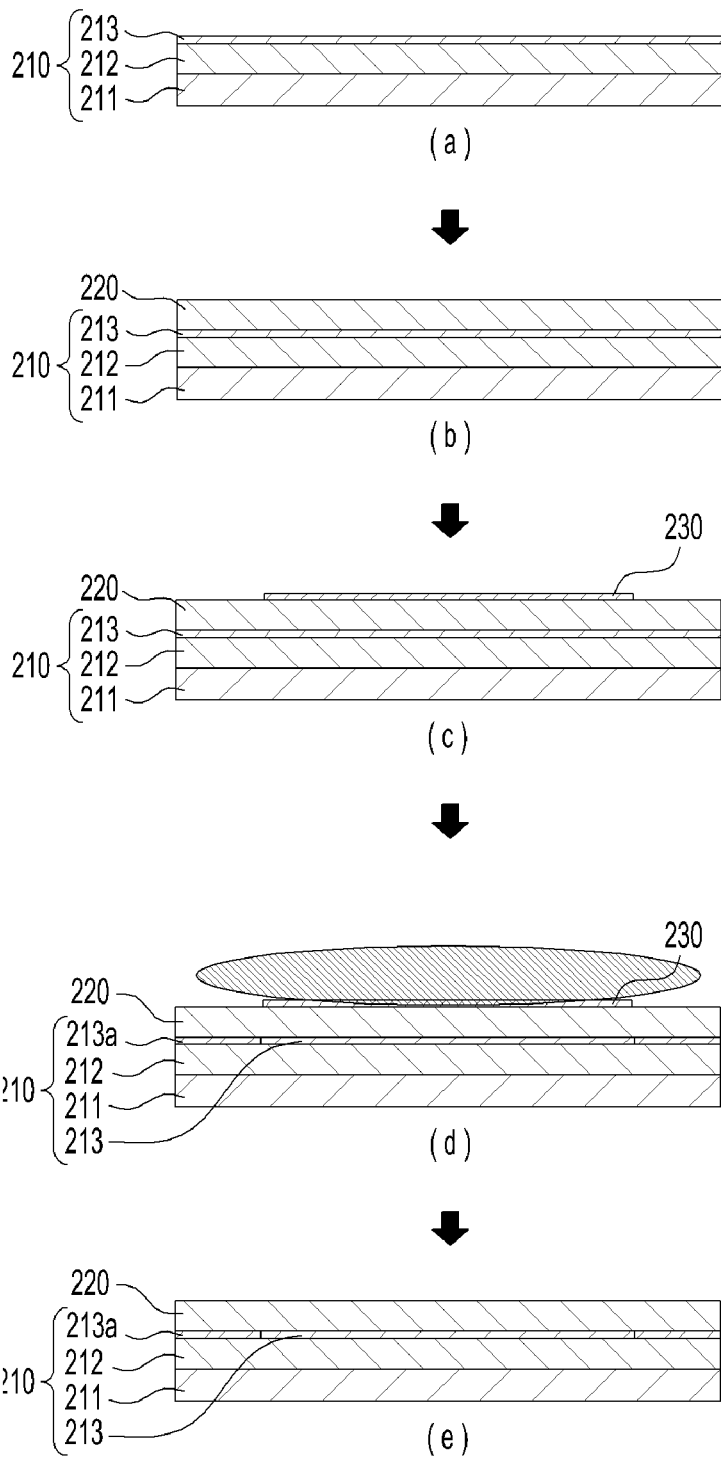
FIG. 5 is a view illustrating processes of a step of performing preparation and the step of performing the adhesion according to the embodiment of the present invention.

FIG. 3 is a flowchart of a method for manufacturing the balloon type retinal stimulation device according to the embodiment of the present invention, FIG. 4 is a flowchart of a step of performing adhesion according to the embodiment of the present invention, and FIG. 5 is a view illustrating processes of a step of performing preparation and the step of performing the adhesion according to the embodiment of the present invention.

As illustrated in FIGS. 3 to 5, in the method for manufacturing a balloon type retinal stimulation device 200, first, Step S210 of preparing a lower substrate and an upper substrate can be performed.

In Step S210 of preparing the lower substrate and the upper substrate, as illustrated in (a) of FIG. 5, first, the lower substrate 210 can be provided to be prepared by forming a first spin-coated PDMS(polydimethylsiloxane) layer 212 over a carrier substrate 211 and forming a first Parylene layer 213 by applying Parylene over the first spin-coated PDMS layer 212 so as to be coupled thereto.

As illustrated in (b) of FIG. 5, the upper substrate 220 can be provided to be prepared by forming a second spin-coated PDMS layer 220 over the first Parylene layer 213.

Here, the lower substrate 210 and the upper substrate 220 can be prepared simultaneously, or the upper substrate 220 can be prepared before the lower substrate 210.

In addition, the lower substrate 210 and the upper substrate 220 correspond to the substrate unit 110 of the balloon type retinal stimulation device 100.

After Step S210 of preparing the lower substrate and the upper substrate, Step S220 of performing adhesion of the prepared upper substrate and lower substrate can be performed.

After Step S220 of performing the adhesion of the prepared upper substrate and lower substrate, first, Step S221 of forming first masking patterns over the prepared upper substrate is performed.

In Step S221 of forming the first masking patterns over the prepared upper substrate, the first masking patterns 230 can be formed to have pattern shapes at parts at which the upper substrate 220 and the lower substrate 210 are not bonded to each other, as illustrated in (c) of FIG. 5.

In other words, when the upper substrate 220 and the lower substrate 210 adhere to each other, the adhering positions can be determined depending on the pattern shapes of the first masking patterns 230.

After Step S221 of forming the first masking patterns over the prepared upper substrate, Step S222 of irradiating the first masking patterns with plasma can be performed.

In Step S222 of irradiating the first masking patterns with plasma, the plasma with which irradiation is performed toward the first masking patterns 230 enables the first Parylene layer 213 positioned at an outer side of the first masking patterns 230 to adhere to the upper substrate 220, as illustrated in (d) of FIG. 5.

In other words, the plasma with which the irradiation is performed toward the first Parylene layer 213 can activate parts which are not blocked by the first masking patterns 230 such that the upper substrate 220 and the lower substrate 210 adhere to each other.

In addition, the plasma can be N.sub.2/O.sub.2 plasma; however, the plasma is not limited thereto.

After Step S222 of irradiating the first masking patterns with plasma, Step S223 of removing the first masking patterns can be performed, as illustrated in (e) of FIG. 5.

Figure 7:
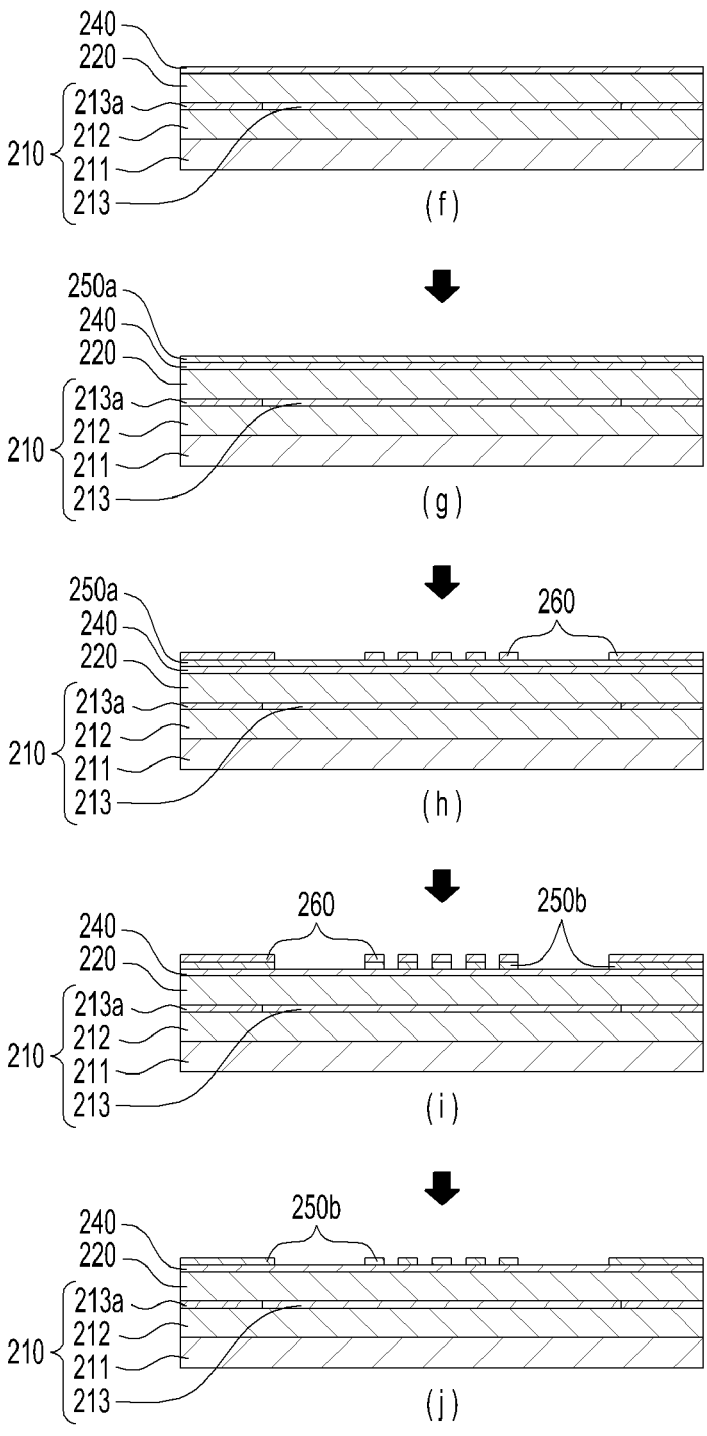
FIG. 7 is a view illustrating processes of the step of forming the metal electrode layer according to the embodiment of the present invention.

FIG. 6 is a flowchart of a step of forming a metal electrode layer according to the embodiment of the present invention, and FIG. 7 is a view illustrating processes of the step of forming the metal electrode layer according to the embodiment of the present invention.

As illustrated in FIGS. 3, 6, and 7, after Step S220 of performing the adhesion of the prepared upper substrate and lower substrate, Step S230 of forming the metal electrode layer above the adhesion-performed upper substrate can be performed.

Besides, in Step S230 of forming the metal electrode layer above the adhesion-performed upper substrate, first, Step S231 of forming a second Parylene layer by applying Parylene over the upper substrate can be performed.

In Step S231 of forming the second Parylene layer by applying Parylene over the upper substrate, a second Parylene layer 240 can be formed by applying Parylene over the upper substrate 210, the Parylene being provided for applying a metal electrode, as illustrated in (f) of FIG. 7.

After Step S231 of forming the second Parylene layer by applying Parylene over the upper substrate, Step S232 of forming a metal thin-film layer by applying a metal thin-film over the second Parylene layer can be performed.

In Step S232 of forming the metal thin-film layer by applying the metal thin-film over the second Parylene layer, the metal thin-film is applied over the second Parylene layer 240, and thereby a metal thin-film layer 250*a* can be formed, as illustrated in (g) of FIG. 7.

Here, the metal thin-film of the metal thin-film layer 250*a* can contain Cr, Ti, Au, Pt, Ir, or the like.

In addition, when the metal thin-film is applied to form the metal thin-film layer 250*a*, a sputter and an evaporator can be used.

After Step S232 of forming the metal thin-film layer by applying the metal thin-film over the second Parylene layer, Step S233 of forming second masking patterns over the applied metal thin-film can be performed.

In Step S233 of forming the second masking patterns over the applied metal thin-film, second masking patterns 260 can be formed over the metal thin-film layer 250*a*, as illustrated in (h) of FIG. 7.

The second masking patterns 260 can be provided to form a metal electrode layer 250*b* by patterning the metal thin-film layer 250*a*, and to this end, the second masking patterns

260 can be provided to have pattern shapes corresponding to a preset shape of the metal electrode layer 250*b*.

After Step S233 of forming the second masking patterns over the applied metal thin-film, Step S234 of forming the metal electrode layer by patterning the metal thin-film layer by using the second masking patterns can be performed.

In Step S234 of forming the metal electrode layer by patterning the metal thin-film layer by using the second masking patterns, the metal electrode layer 250*b* can be formed by patterning the metal thin-film layer 250*a* according to the second masking patterns 260. More specifically, as illustrated in (i) of FIG. 7, in Step S234 of forming the metal electrode layer by patterning the metal thin-film layer by using the second masking patterns, the metal electrode layer 250*b* can be formed by etching and patterning the metal thin-film layer 250*a* according to the pattern shapes of the second masking patterns 260 through a wet etching process.

The wet etching process is performed on the metal thin-film layer 250*a* in a state where the second masking patterns 260 are settled over the metal thin-film layer, and thus etching of the metal thin-film layer can be rapidly and accurately performed at low costs.

After Step S234 of forming the metal electrode layer by patterning the metal thin-film layer by using the second masking patterns, Step S235 of removing the second masking patterns can be performed, as illustrated in (j) of FIG. 7.

The metal electrode layer 250*b* provided as described above corresponds to the stimulation unit 120 of the balloon type retinal stimulation device 100.

Figure 9:
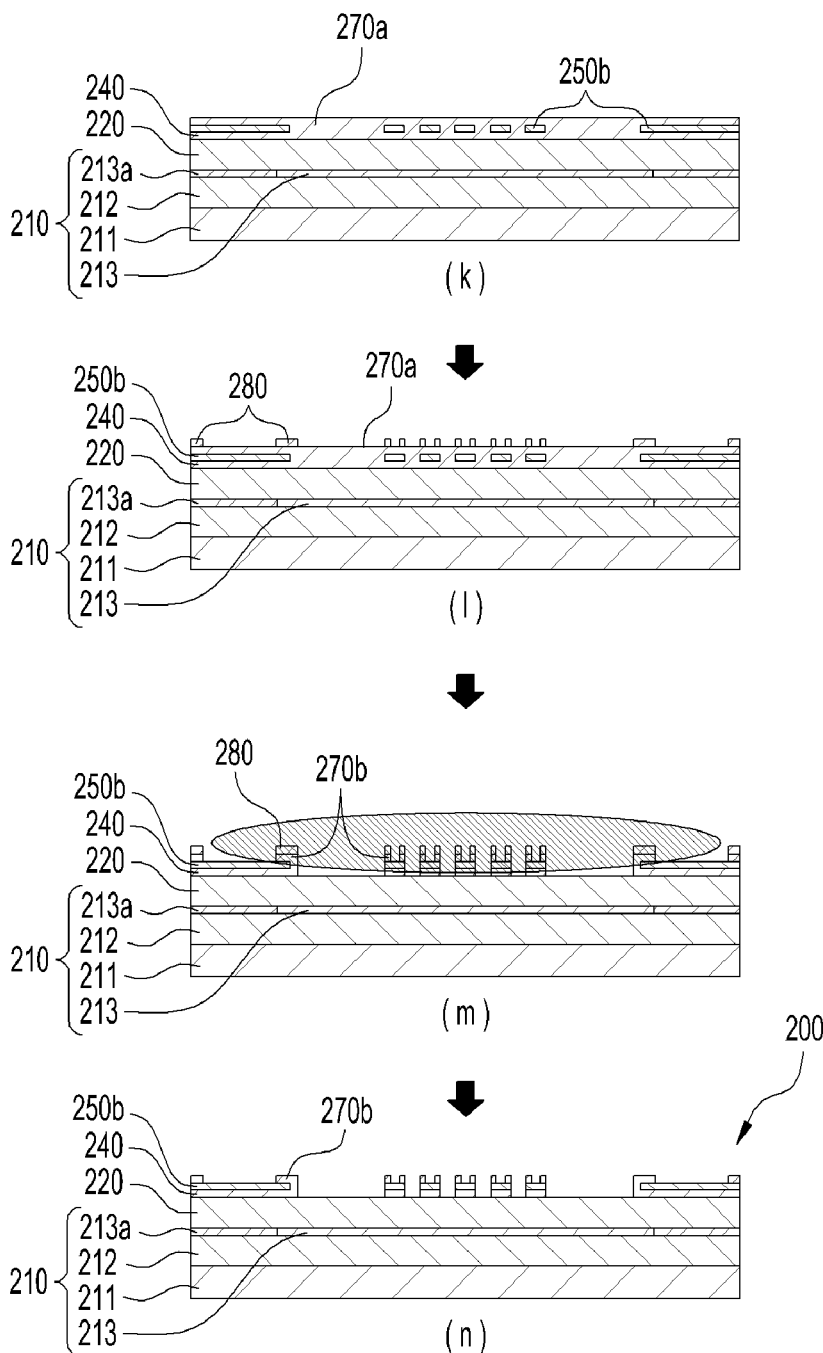
FIG. 9 is a view illustrating processes of the step of forming the insulation layer according to the embodiment of the present invention.

FIG. 8 is a flowchart of a step of forming an insulation layer according to the embodiment of the present invention, and FIG. 9 is a view illustrating processes of the step of forming the insulation layer according to the embodiment of the present invention.

As illustrated in FIGS. 3, 8, and 9, after Step S230 of forming the metal electrode layer above the adhesion-performed upper substrate, Step S240 of forming the insulation layer on the metal electrode layer can be performed.

In Step S240 of forming the insulation layer on the metal electrode layer, first, Step S241 of forming the third Parylene layer by applying Parylene on the metal electrode layer can be performed.

After Step S241 of forming the third Parylene layer by applying Parylene on the metal electrode layer, a third Parylene layer 270*a* can be formed on the metal electrode layer 250*b*. Specifically, the metal electrode layer 250*b* is subjected to the wet etching to form a preset pattern. As illustrated in (k) of FIG. 9, the third Parylene layer 270*a* can be formed by applying Parylene to fill a space formed according to the pattern of the metal electrode layer 250*b* and cover the metal electrode layer 250*b*.

After Step S241 of forming the third Parylene layer by applying Parylene on the metal electrode layer, Step S242 of forming the third masking patterns over the third Parylene layer can be performed.

In Step S242 of forming the third masking patterns over the third Parylene layer, third masking patterns 280 can be formed over the third Parylene layer 270*a*. As illustrated in (1) of FIG. 9, the third masking patterns 280 can be formed into preset patterns such that the third Parylene layer 270*a* can form an insulation layer 270*b*.

After Step S242 of forming the third masking patterns over the third Parylene layer, Step S243 of forming the insulation layer by irradiating the third masking patterns with plasma and etching the third Parylene layer according to pattern shapes of the third masking patterns can be performed.

In Step S243 of forming the insulation layer by irradiating the third masking patterns with plasma and etching the third Parylene layer according to the pattern shapes of the third masking patterns, the insulation layer 270b can be formed by etching the third Parylene layer 270a according to the pattern shapes of the third masking patterns 280 by the plasma with which irradiation is performed toward the third masking patterns 280, as illustrated in (m) of FIG. 9.

The insulation layer 270b provided as described above can be subjected to patterning over a part of the metal electrode layer 250b such that the part of the metal electrode layer 250b can come into contact with a target body such as the retina R. In other words, the insulation layer 270b can perform an insulating function with respect to the metal electrode layer 250b.

In addition, when the metal electrode layer 250b comes into contact with the target body such as the retina R, and the insertion portion 111 is inflated to expand, the stress applied to the metal electrode layer 250b can be reduced by the insulation layer 270b.

Besides, the plasma with which the irradiation is performed to etch the third Parylene layer 270a may be O.sub.2 plasma; however, the plasma is not limited thereto.

In addition, when the balloon type retinal stimulation device 100 expands, the fixing portion 113 which is formed on the circumference of the expanding insertion portion 111 and is provided to prevent expansion comes into close contact with the inner surface of the eyeball that is not the region of retina on which an image is formed so as to function as an anchor, and thereby the fixing portion can fix the metal electrode layer 250b corresponding to the stimulation portion 122 of the balloon type retinal stimulation device 100.

After Step S243 of forming the insulation layer by irradiating the third masking patterns with plasma and etching the third Parylene layer according to the pattern shapes of the third masking patterns, Step S244 of removing the third masking patterns can be performed, as illustrated in (n) of FIG. 9.

After Step S240 of forming the insulation layer on the metal electrode layer, Step S250 of removing a carrier substrate included in the lower substrate can be performed.

Figure 10:
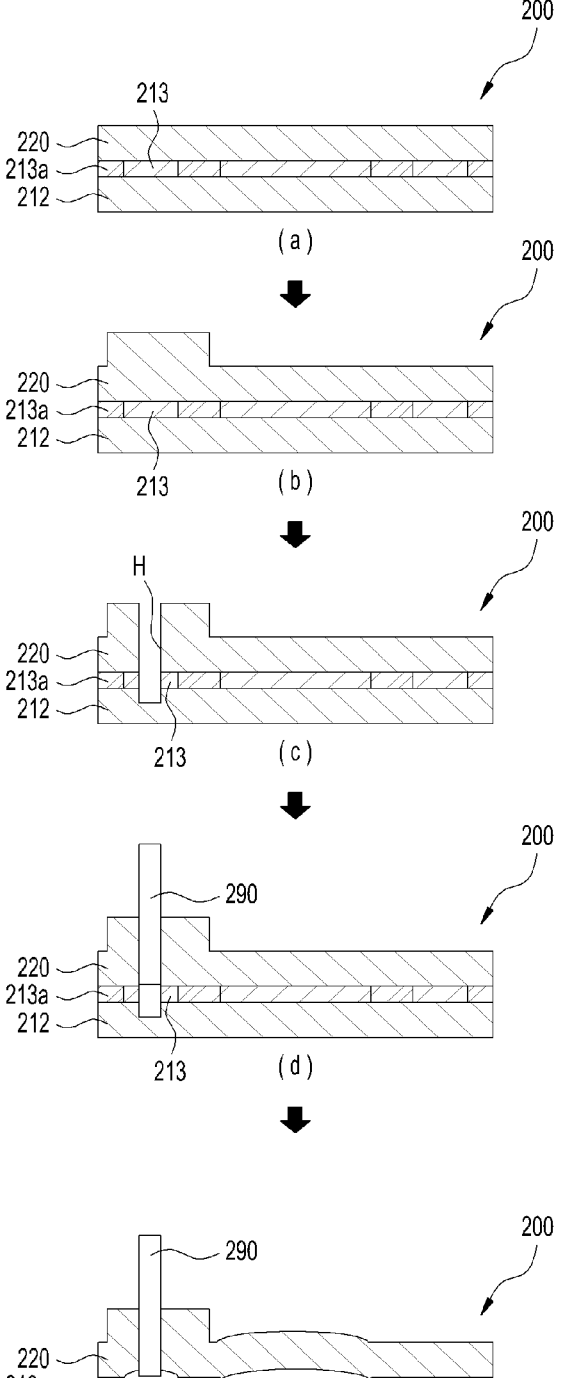
FIG. 10 is a view illustrating processes representing a method for injecting a fluid into the balloon type retinal stimulation device according to the embodiment of the present invention.

FIG. 10 is a view illustrating processes representing a method for injecting a fluid into the balloon type retinal stimulation device according to the embodiment of the present invention.

With reference to FIG. 10, the method for injecting a fluid into the balloon type retinal stimulation device 200 provided as described above is described.

First, the balloon type retinal stimulation device 200 in which the lower substrate 210 and the upper substrate 220 are selectively bonded to each other as described above is prepared. Besides, a through-hole H can be formed at a part of the first Parylene layer 213 at which an adhesive layer 213a is not formed.

The through-hole H can be formed to penetrate the first spin-coated PDMS layer 212 from the upper substrate 220 by a predetermined depth.

Then, an injection port 290 is inserted into the through-hole H, and the lower substrate 210 and the upper substrate 220 can be caused to expand and contract by injecting or discharging a fluid through the injection port 290.

In addition, according to the method provided as described above, the insertion portion 111 of the balloon type retinal stimulation device 100 can expand and contract.

The description of the present invention described above is provided as an example, and a person of ordinary skill in the art to which the present invention belongs can understand that it is possible to easily modify the present invention to another embodiment without altering the technical idea or an essential feature of the present invention. Therefore, the embodiments described above need to be understood as exemplified examples in every aspect and not as examples to limit the present invention. For example, configurational elements described in a singular form can be realized in a distributed manner. Similarly, the configurational elements described in the distributed manner may be realized in a combined manner.

The scope of the present invention needs to be represented by the claims to be described below, and meaning and the scope of the claims and every modification or modified embodiment derived from an equivalent concept of the claims need to be construed to be included in the scope of the present invention.

REFERENCE SIGNS LIST

100 BALLOON TYPE RETINAL STIMULATION DEVICE
110 SUBSTRATE UNIT
111 INSERTION PORTION
112 CHIP INSTALLED PORTION
113 FIXING PORTION
120 STIMULATION UNIT
121 CABLE
122 STIMULATION PORTION
130 CIRCUIT UNIT
200 BALLOON TYPE RETINAL STIMULATION DEVICE
210 LOWER SUBSTRATE
211 CARRIER SUBSTRATE
212 FIRST SPIN-COATED PDMS LAYER
213 FIRST PARYLENE LAYER
213a ADHESIVE LAYER
220 UPPER SUBSTRATE
230 FIRST MASKING PATTERN
240 SECOND PARYLENE LAYER
250a METAL THIN-FILM LAYER
250b METAL ELECTRODE LAYER
260 SECOND MASKING PATTERN
270a THIRD PARYLENE LAYER
270b INSULATION LAYER
280 THIRD MASKING PATTERN
290 INJECTION PORT
H THROUGH-HOLE
R RETINA
V VITREOUS HUMOR
O OUTER LAYER

The invention claimed is:

1. A method for manufacturing a balloon type retinal stimulation device, comprising:
  a) a step of preparing a lower substrate and an upper substrate;
  b) a step of performing adhesion of the prepared upper substrate and lower substrate;
  c) a step of forming a metal electrode layer over the adhesion-performed upper substrate; and
  d) a step of forming an insulation layer on the metal electrode layer,
  wherein, in the step a),
  the lower substrate is provided to be prepared by forming a first spin-coated polydimethylsiloxane (PDMS) layer over a carrier substrate and forming a first Parylene layer by applying Parylene over the first spin-coated PDMS layer, and the upper substrate is provided to be prepared by forming a second spin-coated PDMS layer over the first Parylene layer.

2. The method for manufacturing a balloon type retinal stimulation device according to claim 1, wherein the step b) includes:

b1) a step of forming first masking patterns over the prepared upper substrate;

b2) a step of irradiating the first masking patterns with plasma; and b3) a step of removing the first masking patterns.

3. The method for manufacturing a balloon type retinal stimulation device according to claim 2, wherein, in the step b1), the first masking patterns are formed at sites where the upper substrate and the lower substrate are bonded to each other.

4. The method for manufacturing a balloon type retinal stimulation device according to claim 2, wherein, in the step b2), the plasma with which irradiation is performed to the first masking patterns causes the first Parylene layer positioned at an outer side of the first masking patterns to adhere to the upper substrate.

5. The method for manufacturing a balloon type retinal stimulation device according to claim 2, wherein the step c) includes:

c1) a step of forming a second Parylene layer by applying Parylene over the upper substrate;

c2) a step of forming a metal thin-film layer by applying a metal thin-film over the second Parylene layer;

c3) a step of forming second masking patterns over the applied metal thin-film layer;

c4) a step of forming the metal electrode layer by patterning the metal thin-film layer by using the second masking patterns; and

14 c5) a step of removing the second masking patterns.

6. The method for manufacturing a balloon type retinal stimulation device according to claim 5, wherein, in the step c4), the metal thin-film layer is provided to be patterned into a preset pattern by performing a wet etching process according to pattern shapes of the second masking patterns.

7. The method for manufacturing a balloon type retinal stimulation device according to claim 5, wherein, in the step c4), the metal thin-film layer is provided to be patterned into a preset pattern by performing a lift-off process according to pattern shapes of the second masking patterns.

8. The method for manufacturing a balloon type retinal stimulation device according to claim 5, wherein the step d) includes:

d1) a step of forming a third Parylene layer by applying Parylene on the metal electrode layer;

d2) a step of forming third masking patterns over the third Parylene layer;

d3) a step of forming the insulation layer by irradiating the third masking patterns with plasma and etching the third Parylene layer according to pattern shapes of the third masking patterns; and d4) a step of removing the third masking patterns.

9. The method for manufacturing a balloon type retinal stimulation device according to claim 8, wherein, in the step c3), the third masking patterns are irradiated with O2 plasma.

10. The method for manufacturing a balloon type retinal stimulation device according to claim 1, further comprising:

e) a step of removing a carrier substrate included in the lower substrate after the step d).

* * * * *